US012791542B2

(12) United States Patent
Qahtani et al.

(10) Patent No.: US 12,791,542 B2
(45) Date of Patent: Nov. 10, 2026

(54) SOIL CORROSIVITY TESTING APPARATUS

(71) Applicant: Saudi Arabian Oil Company, Dhahran (SA)

(72) Inventors: Ghazi Salman Qahtani, Al Khobar (SA); Mazyad Alyami, Dammam (SA); Maher Hamed Alerwi, Dhahran (SA); Hassan Hani Alshahdood, Tarout (SA); Mohammed Alshahrani, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 423 days.

(21) Appl. No.: 18/595,142

(22) Filed: Mar. 4, 2024

(65) Prior Publication Data

US 2025/0277777 A1 Sep. 4, 2025

(51) Int. Cl.

| | |
|---|---|
| ***G01N 33/24*** | (2006.01) |
| ***G01N 27/30*** | (2006.01) |
| ***G01S 13/88*** | (2006.01) |

(52) U.S. Cl.

CPC ........... *G01N 33/24* (2013.01); *G01N 27/302* (2013.01); *G01S 13/885* (2013.01)

(58) Field of Classification Search

CPC ..... G01N 27/302; G01N 33/24; G01S 13/885

See application file for complete search history.

(56) References Cited

U.S. PATENT DOCUMENTS 3,621,659 A 11/1971 Anderson et al.
6,144,026 A 11/2000 Udd et al.
(Continued)

FOREIGN PATENT DOCUMENTS

AU 2021221640 9/2022
CA 2832797 5/2018
(Continued)

OTHER PUBLICATIONS

[No Author Listed], "ASTM D698, Standard Test Methods for Laboratory Compaction Characteristics of Soil Using Standard Effort (12,400 ft-lbf/ft$^3$ (600 kN-m/m$^3$))[1], " ASTM International, 2021, 7 pages.
(Continued)

*Primary Examiner* — Gregory H Curran
(74) *Attorney, Agent, or Firm* — Fish & Richardson P.C.

(57) ABSTRACT

Implementations of the present disclosure includes a testing apparatus that includes a base, multiple threaded studs, and a plate. The base has a body defining a flat surface and multiple apertures each arranged to receive an electrode extending through a respective one of the apertures into soil disposed beneath the base. The threaded studs are rotationally coupled to the base. The plate is threadedly coupled to the threaded studs such that rotation of the threaded studs changes an elevation of the plate with respect to the base. The plate includes a lowermost surface facing the base and an uppermost surface facing away from the base and arranged to receive a load. The lowermost surface is coupled to an end of each electrode such that, as the plate changes in elevation, each electrode moves through its respective aperture, changing a position of each electrode with respect to the soil.

20 Claims, 4 Drawing Sheets

(56) References Cited

U.S. PATENT DOCUMENTS

| | | | | |
|---|---|---|---|---|
| 6,885,785 | B2 | 4/2005 | Dunphy et al. | |
| 7,526,944 | B2 | 5/2009 | Sabata et al. | |
| 8,261,601 | B2 | 9/2012 | Stolle et al. | |
| 9,109,988 | B2 | 8/2015 | Morgan et al. | |
| 9,291,543 | B1 | 3/2016 | Robinson et al. | |
| 10,330,586 | B2 | 6/2019 | Ulmer | |
| 11,041,796 | B2 * | 6/2021 | Anderson | G06F 17/15 |
| 11,262,289 | B1 | 3/2022 | Ohodnicki, Jr. et al. | |
| 11,519,894 | B2 | 12/2022 | Teepe et al. | |
| 11,619,576 | B2 | 4/2023 | Kiyono et al. | |
| 2003/0029232 | A1 | 2/2003 | Felix et al. | |
| 2006/0049341 | A1 | 3/2006 | Wang et al. | |
| 2006/0162431 | A1 | 7/2006 | Harris et al. | |
| 2011/0210014 | A1 | 9/2011 | Garosshen | |
| 2014/0247063 | A1 * | 9/2014 | Kawasaki | G01R 27/20 324/691 |
| 2021/0341381 | A1 * | 11/2021 | Mineta | G01N 17/04 |
| 2022/0022362 | A1 | 1/2022 | Anderson, Jr. et al. | |
| 2022/0107170 | A1 | 4/2022 | Chilukuri et al. | |

FOREIGN PATENT DOCUMENTS

| | | |
|---|---|---|
| CN | 201382890 | 1/2010 |
| CN | 102998339 | 3/2013 |
| CN | 110044976 | 7/2019 |
| KR | 20130056589 | 5/2013 |
| KR | 20150025605 | 3/2015 |
| KR | 101519438 | 5/2015 |
| WO | WO 2012170580 | 12/2012 |

OTHER PUBLICATIONS

Abro et al., "Development of FBG pressure sensors using FDM technique for monitoring sleeping postures," Sensors and Actuators A: Physical, Jun. 2021, 331:112921, 8 pages.

Advanced Polyimide Materials, Yang (ed)., 2018, Chapter 5, 61 pages.

Ansari, et al., "Investigation of distributed moisture and temperature measurements in transformers using fiber optics sensors," IEEE Transactions on Power Delivery, Aug. 2019, 34(4):1776-1784, 9 pages.

Atanas Wall loss dependence on strained FBG sensors' simulated response, International Journal of Scientific & Engineering Research, Jun. 2016, 7(6):237-241, 5 pages.

Ban et al., "A novel capacitance sensor for fireside corrosion measurement," Review of Scientific Instruments, 2009, 80(11):115107, 7 pages.

Berruti et al., "A comparative study of radiation-tolerant fiber optic sensors for relative humidity monitoring in high-radiation environments at CERN," IEEE Photonics Journal, Dec. 2014, 6(6):16 pages.

Brondel et al., "Corrosion in the Oil Industry," Oilfield Review, Apr. 1994, 6(2):4-18, 15 pages.

Cetin et al., "Soil structure changes during compaction of a cohesive soil," Engineering Geology, Mar. 13, 2007, 92(1-2):38-48, 11 pages.

Cheng et al., "Simulation of a novel capacitive sensor for rebar corrosion detection," Construction and Building Materials, Apr. 2018, 174:613-624, 12 pages.

Clarke, "Wien Bridge Oscillator Design," Proceedings of the I.R.E., Feb. 1953, 41(2):246-249, 4 pages.

Fan et al., "Review of fiber optic sensors for corrosion monitoring in reinforced concrete," Cement and Concrete Composites, Mar. 2021, 120:104029, 19 pages.

Fang et al., "Application of Embedded Fiber Bragg Grating (FBG) Sensors in Monitoring Health to 3D Printing Structures," IEEE Sensors Journal, Sep. 2016, 16(17):6604-6610, 7 pages.

Feng et al., "Effects of CO2 and H2S on Corrosion of Martensitic Steels in Brines at Low Temperature," Mar. 2018, Corrosion, 74(3):276-287, 12 pages.

Feng et al., "Electrochemical Corrosion of Ultra-High Strength Carbon Steel in Alkaline Brines Containing Hydrogen Sulfide," Electrochima Acta, Sep. 2016, 212:998-1009, 12 pages.

Gu, et al., "A novel capacitive-type humidity sensor using CMOS fabrication technology," Sensors and Actuators B: Chemical, May 2004, 99(2-3):491-498, 8 pages.

Harrey et al., "Capacitive-type humidity sensors fabricated using the offset lithographic printing process," Sens. Actuators B, Dec. 2002, 87(2):226-232, 7 pages.

Hu et al., "Visualization and quantification of soil laboratory impact compaction," Journal of Rock Mechanics and Geotechnical Engineering, Aug. 2, 2021, 14(2):616-624, 9 pages.

Kang et al., "A High-Speed Capacitive Humidity Sensor with On-Chip Thermal Reset," IEEE Trans. Electron Devices, Apr. 2000, 47(4):702-709, 9 pages.

Kirianaki et al., Data acquisition and signal processing for smart sensors, Mar. 2002, pp. 51-60, 10 pages.

Kraus et al., "Plasmapolymerized silicon organic thin films from HMDSN for capacitive humidity sensors," Sensors and Actuators B: Chemical, Feb. 2003, 88(3):300-311, 12 pages.

Kronenberg et al., "Relative humidity sensor with optical fiber Bragg gratings," Optics Letters, Aug. 2002, 27(16): 1385-1387, 3 pages.

Kuzubasoglu, Recent Studies on the Humidity Sensor: A Mini Review. ACS Applied Electronic Materials, 2022, 4(10):4797-4807, 11 pages.

Lee et al., "Humidity Sensors: A Review," Sensor Letters, 2005, 3(1):14 pages.

Liu et al., "Corrosion of underground pipelines in clay soil with varied soil layer thicknesses and aerations," Arabian Journal of Chemistry, Dec. 2, 2019, 13, 3601-3614, 14 pages.

Lu et al., " A Multifunctional Fiber Optic Sensor for Internal Corrosion Monitoring In Natural Gas Transmission Pipelines " Corrosion Conferences & Expo, 2018, Phoenix, Arizona, Apr. 2018, 12 pages.

Morison, "Remote Monitoring of Pipeline Corrosion Using Fiber Optic Sensors," NACE-08290, NACE International Corrosion Conference & Expo, 2018, 9 pages.

Najeeb et al., "Organic Thin-Film Capacitive and Resistive Humidity Sensors: A Focus Review" Advanced Materials Interfaces, Sep. 2018, 5(21):18009691, 19 pages.

Nishio "Quality Evaluation of Fiber-Optic Strain Data Acquired in Long-Term Bridge Monitoring," Sensors and Materials, 2017, 29(2):141-152, 12 pages.

Okafor et al., "Effect of Acetic Acid on CO2 Corrosion of Carbon Steel in Vapor-Water Two-Phase Horizontal Flow," Chem. Eng. Commun., Feb. 2007, 194(2):141-157, 17 pages.

Oliva et al., "Temperature coefficient of resistance and thermal expansion coefficient of 10-nm thick gold films," Thin Solid Films, Feb. 2017, 623:84-89, 27 pages.

Park et al., "Enhanced Moisture-Reactive Hydrophilic-PTFE-Based Flexible Humidity Sensor for Real-Time Monitoring," Sensors, 2018, 18(3):921, 9 pages.

Rafefi, "Development of Thin Film Electrical Resistance Sensors For In Situ Monitoring of Top of the Line Corrosion," Thesis for the degree of Doctor of Philosophy, University of Manchester, 2020, 341 pages.

Rustandi et al., "Corrosion rate of carbon steel for flowline and pipeline as transmission pipe in natural gas production with CO2 content," Makara Journal of Technology, Apr. 2012, 16(1): 57-62, 6 pages.

Sarma et al., "A real-time data acquisition system for monitoring sensor data," Int. J. Comput. Sci. Eng, Jun. 2018, 6(6):539-542, 5 pages.

Singer et al., "Experimental study of sour top-of-the-line corrosion using a novel experimental setup," Corrosion, Jun. 2013, 69:624-638, 15 pages.

Singer et al., "Sour top-of-the-line corrosion in the presence of acetic acid," Corrosion, Aug. 2011, 67(8):085003-1-085003-16, 16 pages.

Sridharan et al., "Mini Compaction Test Apparatus for Fine Grained Soils," ASTM Geotechnical Testing Journal, May 2005, 28(3): 240-246, 7 pages.

(56) References Cited

OTHER PUBLICATIONS

Tai et al., "Paper-Based Sensors for Gas, Humidity, and Strain Detections: A Review," ACS Appl. Mater. Interfaces, 2020, 12, 28, 31037-31053, 66 pages.
Tan et al., "Detection, visualization, quantification, and warning of pipe corrosion using distributed fiber optic sensors," Automation in Construction, Dec. 2021, 132(18):103953, 38 pages.
Wasim et al., "Corrosion behaviour of pipes in soil and in simulated soil solution," Corrosion and Prevention, Nov. 2017, 12 pages.
Wright et al., "Electrolessly coated optical fibers for distributed corrosion monitoring," In Corrosion, Mar. 24-28, 2019, Nashville, TN, 19 pages.
Wright et al., "Metallic Film-Coated Optical Fiber Sensor for Corrosion Monitoring at High Pressures," In AMPP Annual Conference+ Expo in San Antonio, Texas, Paper No. 17804, Mar. 6-10, 2022, 11 pages.
Wright et al., "Effect of HCO3—on Electrochemical Kinetics of Carbon Steel Corrosion in CO2-Saturated Brines," Electrochim. Acta, Nov. 2018, 290:626-638, 45 pages.
Xu et al., "Development of a real-time AC/DC data acquisition technique for studies of AC corrosion of pipelines" Corrosion Science, 2012, 61: 215-223, 9 pages.
Yeo et al., "Characterisation of a polymer-coated fibre Bragg grating sensor for relative humidity sensing," Sensors and Actuators B: Chemical, 2005, 110(1):148-156, 8 pages.
Zhang et al., "Ultrasensitive skin-like wearable optical sensors based on glass micro/nanofibers," Opto-Electronic Advances, 2020, 3(3):190022-1-190022-7, 7 pages.

* cited by examiner

SOIL CORROSIVITY TESTING APPARATUS

TECHNICAL FIELD

This disclosure relates soil corrosivity testing systems.

BACKGROUND

Soil can be tested for corrosivity to determine the extent of corrosive soil and corrosive water for oil production purposes. Three-electrode electrochemical systems use electrochemical reactions to measure the concentration of chemicals in the soil and thereby determine the corrosivity of the soil. Methods and equipment for improving corrosivity testing are sought.

SUMMARY

Implementations of the present disclosure include a testing assembly that includes a beaker, a sample holder, soil, a sample specimen, a three-electrode testing assembly, an electrochemical analyzer, and a laser assembly. The sample holder is disposed at a bottom surface of the beaker. The soil is disposed within the beaker and on the sample holder. The sample specimen is disposed on the sample holder. The three-electrode testing assembly is disposed partially within the beaker and on the soil. The three-electrode testing assembly includes a base, multiple threaded knobs, and a plate. The base has a body defining a flat surface arranged to bear against and compact the soil. The base defines multiple apertures each arranged to receive an electrode extending through a respective one of the apertures into the soil. The threaded knobs are rotationally coupled to the base and extend from the base normal with respect to the flat surface of the base. The plate is threadedly coupled to the threaded knobs such that rotation of the threaded knobs changes an elevation of the plate with respect to the base. The plate has a lowermost surface facing the base and an uppermost surface facing away from the base and arranged to receive a load. The lowermost surface is coupled to an end of each electrode such that, as the plate changes in elevation with respect to the base, each electrode moves through its respective aperture, changing a position of each electrode with respect to the soil. The electrochemical analyzer is electrically coupled to each electrode and processes information received from each electrode and determines, as a function of the information, an electrochemical corrosion of the sample specimen. The laser assembly includes a laser emitter and a laser reflector. The laser emitter is coupled to an outer wall of the beaker and includes an electronic display. The laser reflector is coupled to the plate and is aligned with the laser emitter such that the laser reflector reflects a laser emitted from the laser emitter to the laser emitter, allowing the laser emitter toa allow the emitter to detect the reflected laser and determine, as a function of the reflected laser, a distance between the laser emitter and the laser reflector.

In some implementations, the laser emitter includes a microcontroller, an electronic display, and a power source configured to power the electronic display. The microcontroller determines the distance as the distance changes as the three-electrode testing assembly compacts the soil under the load. The electronic display displays the distance in real time. In some implementations, the microcontroller determines, as a function of the determined distance, when a reduction in distance stabilizes, indicating that compaction is completed. The laser reflector further includes a speaker that emits a sound when the microcontroller determines that compaction is completed.

In some implementations, the three-electrode testing assembly includes a ground-penetrating radar (GPR) coupled to the base. The GPR generates and transmit subsurface images to a processing device and the processing device determines, as a function of the subsurface images, at least one of a compaction level of the soil or a moisture level of the soil.

In some implementations, the plate includes an indentation at a center of the plate to support a weight applying the load and prevent the weight from shifting along the uppermost surface of the plate, allowing the load to be applied uniformly over a period of compaction.

Implementations of the present disclosure includes a testing apparatus that includes a base, multiple threaded studs, and a plate. The base has a body defining a flat surface and multiple apertures each arranged to receive an electrode extending through a respective one of the apertures into soil disposed beneath the base. The threaded studs are rotationally coupled to the base and extend from the base normal with respect to the flat surface of the base. The plate is threadedly coupled to the threaded studs such that, with the testing apparatus assembled, rotation of the threaded studs changes an elevation of the plate with respect to the base. The plate includes a lowermost surface facing the base and an uppermost surface facing away from the base and arranged to receive a load. The lowermost surface is arranged to be coupled to an end of each electrode such that, as the plate changes in elevation with respect to the base, each electrode moves through its respective aperture, changing a position of each electrode with respect to the soil.

In some implementations, the testing apparatus further includes a beaker configured to hold a sample with the soil inside the beaker and on the sample. The body of the base defines a flat surface arranged to bear against and compact the soil.

In some implementations, the body includes a circular body defining a diameter corresponding with an inner diameter of the beaker such that the circular body is movable, with the flat surface parallel with respect to a base of the beaker, along the beaker to allow the circular body to move toward the base of the beaker and compact, under the load, the soil between the sample, the flat surface, and an inner wall of the beaker.

In some implementations, the testing apparatus further includes a sample holder arranged to rest on the base of the beaker and includes an indentation that holds the sample and prevents the sample from shifting along an upper surface of the sample holder.

In some implementations, the testing apparatus includes a three-electrode testing assembly. Each electrode is electrically coupled to an electrochemical analyzer configured to process information received from each electrode and determine, as a function of the information, an electrochemical corrosion of the sample.

In some implementations, the apertures include four or more apertures, including a first aperture configured to receive a reference electrode, a second aperture configured to receive a working electrode, a third aperture configure to receive a counter electrode, and a further aperture configured to receive an instrument including at least one of a thermocouple or a pH measurement instrument.

In some implementations, the testing apparatus also includes a laser assembly that includes a laser emitter arranged to be coupled to an outer wall of the beaker and include an electronic display. The laser reflector is coupled to the plate and aligned with the laser emitter such that a laser emitted from the laser emitter reflects back to the laser emitter, allowing the laser emitter to detect the reflected laser and determine, as a function of the reflected laser, a distance between the laser emitter and the laser reflector to determine a distance that the soil compacts under the load.

In some implementations, the laser emitter includes a microcontroller, an electronic display, and a power source configured to power the electronic display. The microcontroller determines the distance as the distance changes as the three electrode testing assembly compacts the soil under the load. The electronic display displays the distance in real time.

In some implementations, the microcontroller determines, as a function of the determined distance, when a reduction in distance stabilizes, indicating that compaction is completed. The laser reflector further includes a speaker configured it emit a sound when the compaction is completed.

In some implementations, the testing assembly further includes a ground-penetrating radar (GPR) coupled to the base, the GPR generates and transmits subsurface images to a processing device and the processing device determines, as a function of the subsurface images, at least one of a compaction level of the soil or a moisture level of the soil.

In some implementations, the plate includes an indentation at a center of the plate to support a weight applying the load and prevent the weight from shifting along the uppermost surface of the plate, allowing the load to be applied uniformly over a period of compaction.

In some implementations, rotation of the studs changes an elevation of the plate without changing an elevation of the screws with respect to the base.

In some implementations, the threaded studs include threaded knobs, each of the threaded knobs spaced apart equidistantly from one another.

Implementations of the present disclosure include a method that includes obtaining a testing apparatus that includes a base, threaded studs, and a plate. The base includes a body defining a flat surface and apertures each arranged to receive an electrode extending through a respective one of the apertures into soil disposed beneath the base. The threaded studs are rotationally coupled to the base and extend from the base normal with respect to the flat surface of the base. The plate is threadedly coupled to the studs such that rotation of the studs changes an elevation of the plate with respect to the base. The plate includes a lowermost surface facing the base and coupled to an end of each electrode such that, as the plate changes in elevation with respect to the base, each electrode moves through its respective aperture, changing a position of each electrode with respect to the soil. The method also includes placing a sample specimen inside a beaker. The method also includes placing the soil inside the beaker and on the sample specimen. The method also includes placing the testing apparatus on the soil with at least one electrode extending into the soil. The method also includes placing a weight on the plate to apply a load on the testing apparatus, allowing the testing apparatus to compact the soil under the load as each electrode detects a parameter of the sample specimen or the soil.

In some implementations, the method further includes including rotating the threaded studs as the testing apparatus compacts the soil, moving each electrode with respect to the base to maintain a desired distance between a tip of each electrode and the sample specimen.

Particular implementations of the subject matter described in this specification can be implemented so as to realize one or more of the following advantages. For example, the testing assembly of the present disclosure allows compaction of the soil without requiring manual compaction, and while the testing apparatus tests for soil corrosivity. Also, the testing apparatus allows consistent compaction of the soil, which can result in more accurate testing results. Moreover, the testing apparatus allows the accurate monitoring and control of the compaction process, ensuring uniformity and consistency across multiple experimental trials. In addition, the laser feature offers a wider range of compact levels, allowing for a more accurate simulation of actual soil conditions found in the field. This can increase the accuracy and consistency of laboratory tests, broaden the scope and utility of the testing apparatus, and allow a wider range of soil conditions to be accurately tested.

DETAILED DESCRIPTION OF THE DISCLOSURE

Figure 1:
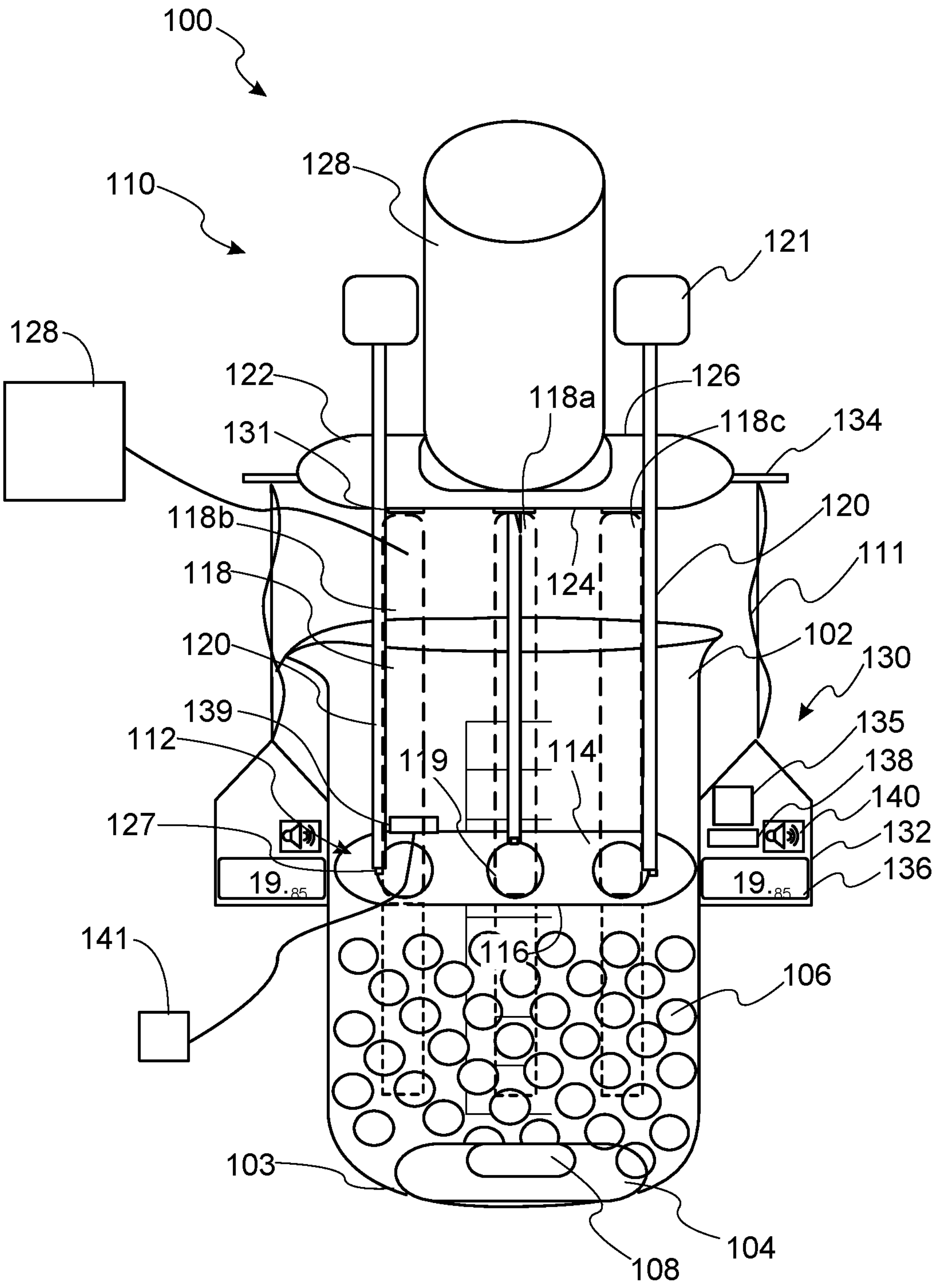
FIG. 1 shows front schematic view of a testing assembly.

FIG. 1 shows a compaction and testing assembly 100 (e.g., a three-electrode system or soil corrosivity evaluation device) that includes a beaker 102, a sample holder 104, a sample 108 (e.g., a metal specimen or coupon), soil 106, a testing apparatus 110 (e.g., a three-electrode cell or testing assembly), and a laser assembly 130. The testing assembly 100 can perform a corrosivity test while at the same time compact the soil uniformly.

In some aspects, the sample holder 104 is disposed at a bottom surface 103 (e.g., the base) of the beaker 102. The sample 108 rests on the sample holder 104. During the corrosivity test, the soil 106 resides within the beaker 102 between the sample holder 104 and the testing apparatus 110. During the test, the testing apparatus 110 resides partially within the beaker 102 and sits on the soil 106 to compress the soil 106.

The testing apparatus 110 includes a base 112, multiple threaded studs 120 (e.g., threaded knobs with handles 121), and a plate 122. The base 112 of the testing apparatus 110 has a circular body 114 that defines a flat surface 116 that bears against and compacts the soil 106. The body has multiple apertures 119 each arranged to receive an electrode 118 (shown in dashed lines for clarity) extending through a respective one of the apertures 119 into the soil 106. For example, one of the apertures 119 (e.g., the central aperture) receives a reference electrode 118*a*, a second aperture 119 receives a working electrode 118*b*, and a third aperture 119 receives a counter electrode 118*c*. As further described in detail below with respect to FIG. 2. the circular body 114 can have more than three holes 119 to accommodate more instruments.

In some aspects, the testing apparatus 110 also includes an electrochemical analyzer 128 electrically coupled to each electrode 118. The electrochemical analyzer 128 processes information received from each electrode 118 and determines, as a function of the information, the corrosivity of the soil 106 or the electrochemical corrosion of the sample 108. In some aspects, the electrochemical analyzer 128 also determines other parameters of the sample or soil or both, such as the concentration of various chemicals in the soil.

The threaded studs 120 are rotationally coupled to the base 112 and extend from the base 112 in a direction normal (e.g., perpendicular) with respect to the flat surface 116 of the base 112. The threaded studs are attached (e.g., with a rotational bearing attachment 127) to the body 114 of the base 112 to allow rotation of the studs 120 without screwing in or out the screws from the body 114.

The plate 122 as threaded holes 131 that correspond to the locations of each threaded stud 120. The threaded holes 131 extend through the plate 122 and allow the plate 122 to be threadedly attached to each threaded stud 120 such that rotation of the threaded studs 120 changes an elevation of the plate 122 with respect to the base 112. The plate 122 has a lowermost surface 124 facing the base 112 and an uppermost surface 126 facing away from the base 112. The uppermost surface 126 supports a weight 128 that applies a load on the testing apparatus 110 to compact the soil 106. The lowermost surface 124 is coupled (e.g., through a mechanical fastener 113 or an adhesive or the like) to an end of each electrode 118 such that, as the plate 122 changes in elevation with respect to the base 111, each electrode 118 moves along its respective aperture 119, changing a position (e.g., the depth) of each electrode 118 within the soil 116.

In some aspects, the threaded studs 120 are rotatable to lift the plate 122 with respect to the base 112 as the soil is compacted, allowing an operator to prevent the electrodes 118 from touching the bottom surface 103 of the beaker 102. For example, to keep the reference electrode 118*a* facing the sample 108 as close as possible (and thus ensure appropriate electrochemical measurements), an operator can rotate, as the soil 106 is compacted, the threaded studs 120 to lift the plate 122 and thereby the electrodes 118, maintaining the reference electrode 118 at a desired distance from the sample 108.

The laser assembly 130 has a laser emitter 132 (e.g., a transceiver) and a laser reflector 134. In some aspects, the laser emitter 132 is attached to an outer wall of the beaker 102. For example, the laser reflector 134 can be attached to the beaker 102 with an adhesive, a mechanical fastener, or the like. The laser reflector 134 is coupled to the plate 122 and is vertically aligned with the laser emitter 132 such that a laser 111 emitted from the laser emitter 132 reflects back from the reflector 132 to the laser emitter 132. This allows the laser emitter 132 to detect the reflected laser 111 and determine, as a function of the reflected laser 111, a distance between the laser emitter 132 and the laser reflector 134.

In some aspects, the laser emitter 132 has an electronic display 132 (e.g., a digital screen), a power source 138 (e.g., a battery), a microcontroller 135, and a speaker 140. The power source 138 powers the electronic display 136. The microcontroller 135 determines, as a function of the emitter detecting the reflected laser, the distance between the laser emitter 132 and the laser reflector 134. For example, the microcontroller 135 has a processor that receives information form a receiver of the emitter 132 and that the receiver transmits to the processor in response to receiving or sensing the reflected laser. In some aspects, the microcontroller 138 determines, in real time, the distance as the distance changes during compaction of the soil 106. The electronic display 136 displays the distance as the distance chances. For example, the electronic display 126 display the distance in real time as the distance between the plate 122 and the emitter 132 decreases because of the soil's compaction under the weight 128.

In some aspects, the microcontroller 138 determines, as a function of the determined distance, when a reduction in distance has stabilized, which indicates that compaction is completed. For example, the microcontroller 138 can compare, to a time period threshold, the time period that it takes for the distance to change. Them, the microcontroller 138 determines that the compaction is complete when the determined time period satisfies the threshold. For example, if the threshold is 60 seconds, the microcontroller 138 determines, once the distance remains unchanged for 60 seconds, that the soil 106 has been fully compacted under the load 128. In some aspects, the laser emitter 132 has a speaker connected to and controllable by the the microcontroller 138 to emit a sound when the compaction is completed.

In some aspects, the laser assembly 130 determines the soil compaction with high precision. This feature allows for accurate monitoring and control of the compaction process, ensuring uniformity and consistency across multiple experimental trials. By precisely measuring the reduction in distance, researchers can maintain standardized soil conditions, minimizing variations and external influences that could affect the electrochemical testing.

Moreover, the laser assembly 130 can be used as a leveling mechanism to ensure horizontal leveling of compaction. For example, as shown in FIG. 1, the apparatus can incorporate two pairs of laser emitter and reflector assemblies, one on each side of the beaker 102. If both laser emitters 132 detect the same distance, the laser assembly 130 indicates that the compaction is horizontally leveled. However, if the distances differ, it signifies an uneven compaction that requires adjustment. This allows the electrolyte (e.g., the soil) to distribute evenly. If the soil 106 has a tilted surface, the test can be repeater or adjusted.

In some aspects, the testing apparatus 110 has a ground-penetrating radar (GPR) 139 attached to the base 112. The GPR 139 generates subsurface images of the soil 106 and transmits the images to a processing device 141 which can be past of (or the same as) the electrochemical analyzer 128 or a different processing device. The processing device 141 determines, as a function of the subsurface images, a compaction level of the soil 106 and/or a moisture level of the soil 106.

In some aspects, the GPR 139 has a transmitting and receiving antennas that emit electromagnetic waves at specific frequencies and receive the reflected signals after the waves penetrated the soil 106 and interacted with subsurface objects or boundaries. By acquiring radar data from the field, it becomes possible to replicate soil compaction and moisture levels conditions in a laboratory. The radar data serves as a reference for achieving the desired compaction and moisture levels when conducting experiments or tests in a controlled lab environment. This allows realistic field conditions to be replicated, enhancing the reliability and applicability of laboratory research. Thus, the integration of GRP 139 with the laser assembly 130 provides a comprehensive approach to replicate field soil conditions accurately.

Figure 2:
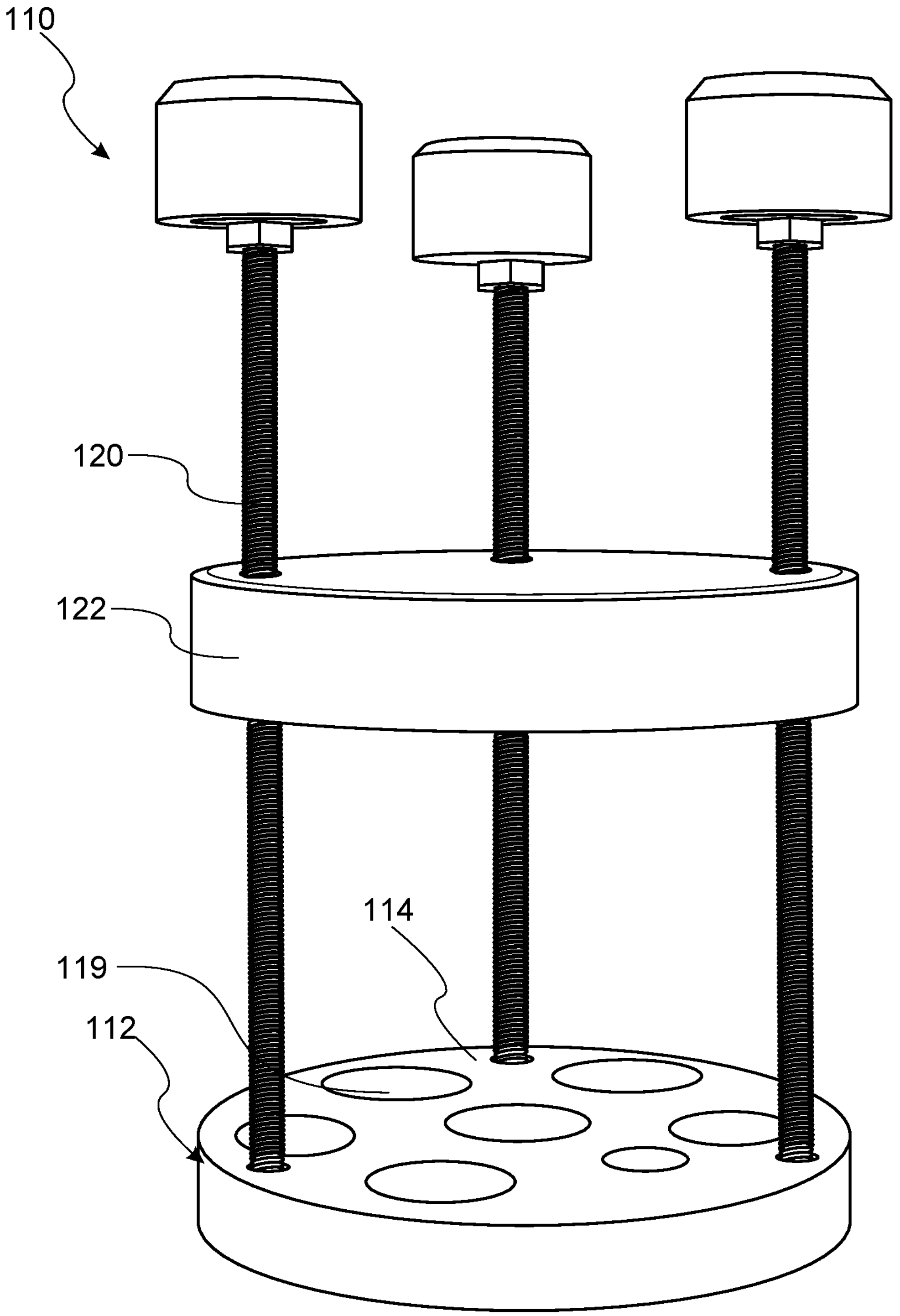
FIG. 2 shows a front perspective view of a testing apparatus of the testing assembly.

FIG. 2 shows a front perspective view of the testing apparatus 110. Referring also to FIG. 1, the body 114 of the base 112 is circular and has a diameter that corresponds with (e.g., is slightly smaller than) an inner diameter of the beaker 102. This allows that the circular body 114 move, with its flat surface 116 parallel with respect to the bottom surface 103 of the beaker 102, along the height of beaker 102. This allows the circular body 114 to move toward the bottom surface 103 of the beaker 102 to compact, under the load of the weight 128, the soil 106 between the sample holder 104, the flat surface 116 of the base 114, and the inner wall of the beaker 102.

In some aspects, the circular body 114 has more than three apertures 119 (e.g., seven apertures) of the same or different sizes. Each aperture receives an instrument that detects a parameter of the soil or the sample. For example, the additional apertures 119 can receive a thermocouple or a pH measurement instrument. Also, as shown in FIG. 2, the threaded studs 120 are spaced apart equidistantly from one another so that the load is evenly distributed among the threaded studs 120.

Figure 3:
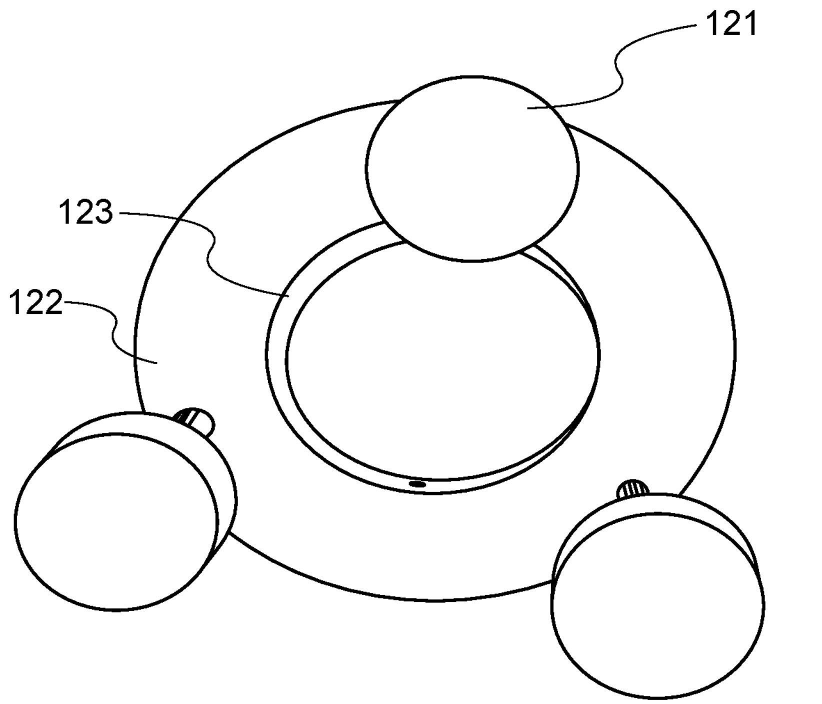
FIG. 3 shows a top view of the testing apparatus.

FIG. 3 shows a top view of the testing apparatus 110. As shown, the plate 122 has a feature that keeps the weight from shifting along the top surface of the plate 122. For example, the plate 122 has an indentation 123 (e.g., a circular groove) at its center to receive the weight 128 and prevent the weight 128 from substantially shifting along the uppermost surface of the plate 122. This allows the load applied by the weight 128 to be applied uniformly on the soil 106 over the period of compaction.

Figure 4:
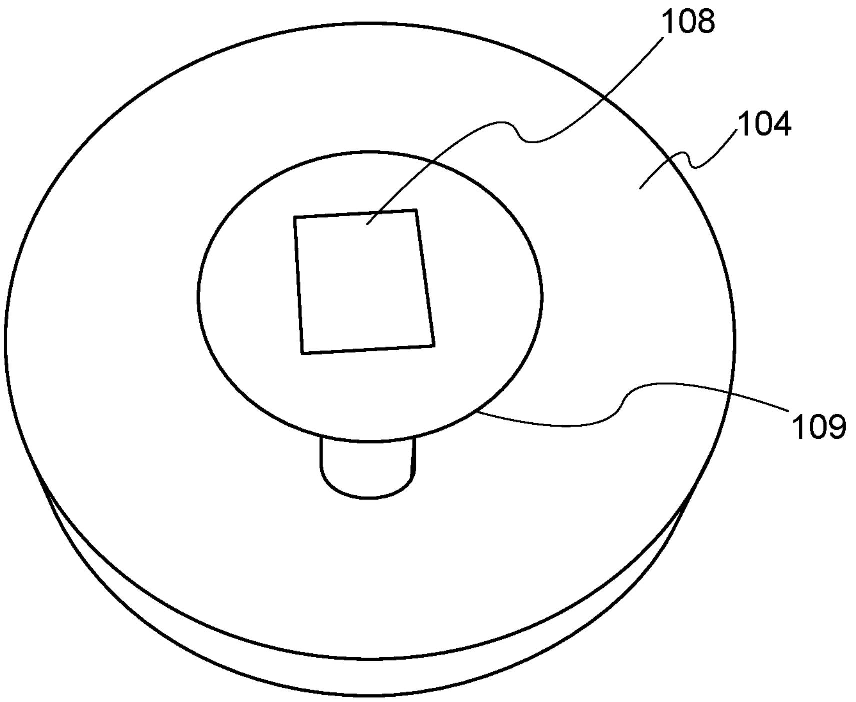
FIG. 4 shows a top schematic view of a sample holder of the testing assembly.

FIG. 4 shows a perspective view of the sample holder 104. Similar to the circular body 122, the sample holder 104 has a diameter that corresponds with (e.g., is slightly smaller than) an inner diameter of the beaker 102. This allows the majority of the sand 106 to rest on the topo surface of the holder 104, preventing substantial soil from falling through the side of the holder 104. In some aspects, the sample holder 104 has an indentation 109 (e.g., a groove) that holds the sample 108 and prevents the sample 108 from shifting along an upper surface of the sample holder 104.

Figure 5:
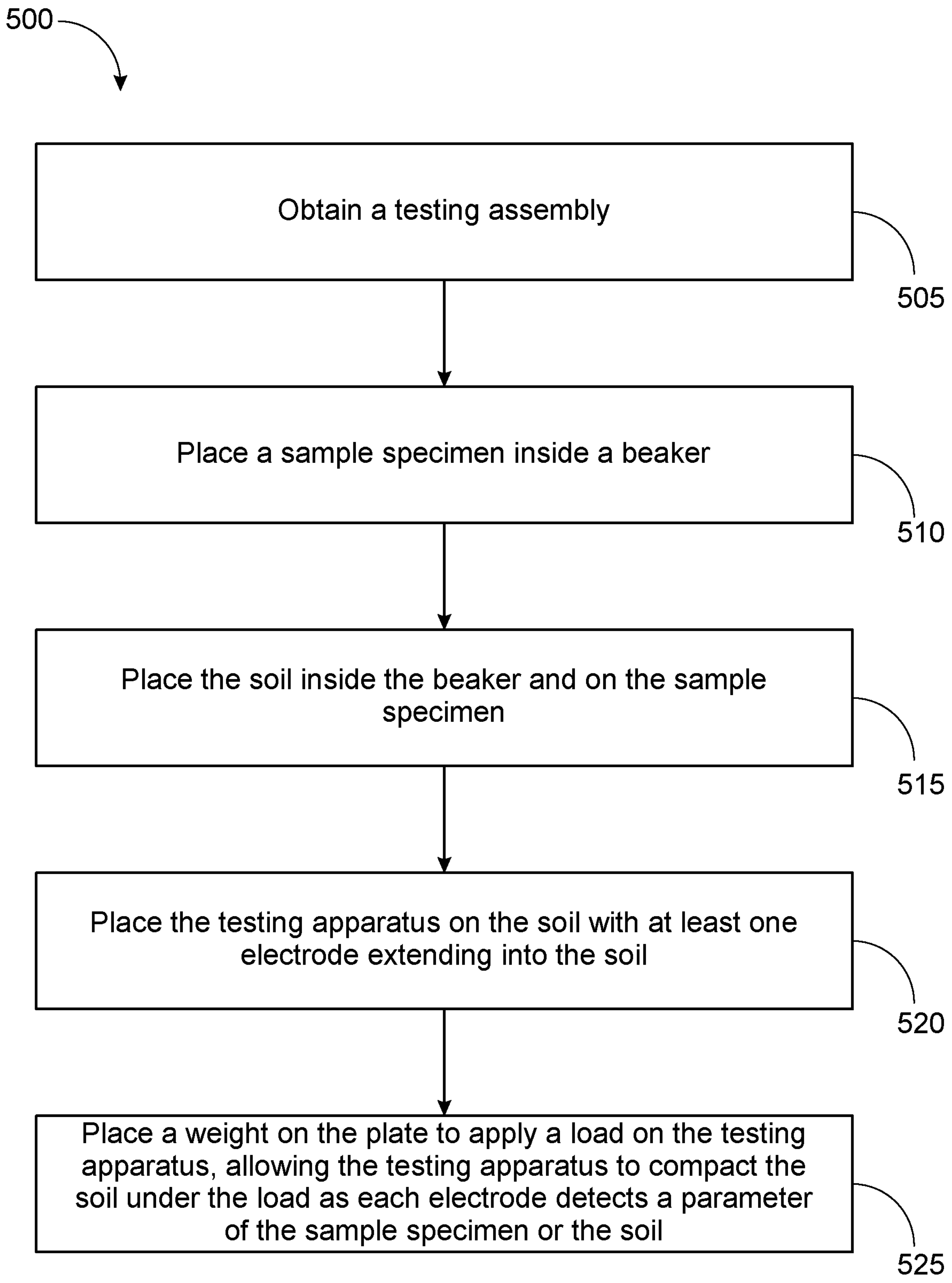
FIG. 5 show a flow chart of an example method of testing soil for corrosivity.

FIG. 5 shows a flow chart of a method (500) of testing soil for corrosivity. The method includes obtaining a testing assembly (505). The testing assembly can be the testing assembly 100 described above with respect to FIGS. 1-4. The method also includes placing a sample specimen inside a beaker (510). The method also includes placing the soil inside the beaker and on the sample specimen (515). The method also includes placing the testing apparatus on the soil with at least one electrode extending into the soil (520). The method also includes placing a weight on the plate to apply a load on the testing apparatus, allowing the testing apparatus to compact the soil under the load as each electrode detects a parameter of the sample specimen or the soil (525).

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

A number of implementations have been described. Nevertheless, it will be understood that various modifications may be made without departing from the spirit and scope of the disclosure. For example, example operations, methods, or processes described herein may include more steps or fewer steps than those described. Further, the steps in such example operations, methods, or processes may be performed in different successions than that described or illustrated in the figures. Accordingly, other implementations are within the scope of the following claims.

EXAMPLES

In an example implementation, a testing assembly includes a beaker, a sample holder, soil, a sample specimen, a three-electrode testing assembly, an electrochemical analyzer, and a laser assembly. The sample holder is disposed at a bottom surface of the beaker. The soil is disposed within the beaker and on the sample holder. The sample specimen is disposed on the sample holder. The three-electrode testing assembly is disposed partially within the beaker and on the soil. The three-electrode testing assembly includes a base, multiple threaded knobs, and a plate. The base has a body defining a flat surface arranged to bear against and compact the soil. The base defines multiple apertures each arranged to receive an electrode extending through a respective one of the apertures into the soil. The threaded knobs are rotationally coupled to the base and extend from the base normal with respect to the flat surface of the base. The plate is threadedly coupled to the threaded knobs such that rotation of the threaded knobs changes an elevation of the plate with respect to the base. The plate has a lowermost surface facing the base and an uppermost surface facing away from the base and arranged to receive a load. The lowermost surface is coupled to an end of each electrode such that, as the plate changes in elevation with respect to the base, each electrode moves through its respective aperture, changing a position of each electrode with respect to the soil. The electrochemical analyzer is electrically coupled to each electrode and processes information received from each electrode and determines, as a function of the information, an electrochemical corrosion of the sample specimen. The laser assembly includes a laser emitter and a laser reflector. The laser emitter is coupled to an outer wall of the beaker and includes an electronic display. The laser reflector is coupled to the plate and is aligned with the laser emitter such that the laser reflector reflects a laser emitted from the laser emitter to the laser emitter, allowing the laser emitter toa allow the emitter to detect the reflected laser and determine, as a function of the reflected laser, a distance between the laser emitter and the laser reflector.

In an example implementation combinable with any other example implementation, the laser emitter includes a microcontroller, an electronic display, and a power source configured to power the electronic display. The microcontroller determines the distance as the distance changes as the three-electrode testing assembly compacts the soil under the load. The electronic display displays the distance in real time.

In an example implementation combinable with any other example implementation, the microcontroller determines, as a function of the determined distance, when a reduction in distance stabilizes, indicating that compaction is completed. The laser reflector further includes a speaker that emits a sound when the microcontroller determines that compaction is completed.

In an example implementation combinable with any other example implementation, the three-electrode testing assembly includes a ground-penetrating radar (GPR) coupled to the base. The GPR generates and transmit subsurface images to a processing device and the processing device determines, as a function of the subsurface images, at least one of a compaction level of the soil or a moisture level of the soil.

In an example implementation combinable with any other example implementation, the plate includes an indentation at a center of the plate to support a weight applying the load and prevent the weight from shifting along the uppermost surface of the plate, allowing the load to be applied uniformly over a period of compaction.

In an example implementation, a testing apparatus includes a base, multiple threaded studs, and a plate. The base has a body defining a flat surface and multiple apertures each arranged to receive an electrode extending through a respective one of the apertures into soil disposed beneath the base. The threaded studs are rotationally coupled to the base and extend from the base normal with respect to the flat surface of the base. The plate is threadedly coupled to the threaded studs such that, with the testing apparatus assembled, rotation of the threaded studs changes an elevation of the plate with respect to the base. The plate includes a lowermost surface facing the base and an uppermost surface facing away from the base and arranged to receive a load. The lowermost surface is arranged to be coupled to an end of each electrode such that, as the plate changes in elevation with respect to the base, each electrode moves through its respective aperture, changing a position of each electrode with respect to the soil.

In an example implementation combinable with any other example implementation, the testing apparatus further includes a beaker configured to hold a sample with the soil inside the beaker and on the sample. The body of the base defines a flat surface arranged to bear against and compact the soil.

In an example implementation combinable with any other example implementation, the body includes a circular body defining a diameter corresponding with an inner diameter of the beaker such that the circular body is movable, with the flat surface parallel with respect to a base of the beaker, along the beaker to allow the circular body to move toward the base of the beaker and compact, under the load, the soil between the sample, the flat surface, and an inner wall of the beaker.

In an example implementation combinable with any other example implementation, the testing apparatus further includes a sample holder arranged to rest on the base of the beaker and includes an indentation that holds the sample and prevents the sample from shifting along an upper surface of the sample holder.

In an example implementation combinable with any other example implementation, the testing apparatus includes a three-electrode testing assembly. Each electrode is electrically coupled to an electrochemical analyzer configured to process information received from each electrode and determine, as a function of the information, an electrochemical corrosion of the sample.

In an example implementation combinable with any other example implementation, the apertures include four or more apertures, including a first aperture configured to receive a reference electrode, a second aperture configured to receive a working electrode, a third aperture configure to receive a counter electrode, and a further aperture configured to receive an instrument including at least one of a thermocouple or a pH measurement instrument.

In an example implementation combinable with any other example implementation, the testing apparatus also includes a laser assembly that includes a laser emitter arranged to be coupled to an outer wall of the beaker and include an electronic display. The laser reflector is coupled to the plate and aligned with the laser emitter such that a laser emitted from the laser emitter reflects back to the laser emitter, allowing the laser emitter to detect the reflected laser and determine, as a function of the reflected laser, a distance between the laser emitter and the laser reflector to determine a distance that the soil compacts under the load.

In an example implementation combinable with any other example implementation, the laser emitter includes a microcontroller, an electronic display, and a power source configured to power the electronic display. The microcontroller determines the distance as the distance changes as the three electrode testing assembly compacts the soil under the load. The electronic display displays the distance in real time.

In an example implementation combinable with any other example implementation, the microcontroller determines, as a function of the determined distance, when a reduction in distance stabilizes, indicating that compaction is completed. The laser reflector further includes a speaker configured it emit a sound when the compaction is completed.

In an example implementation combinable with any other example implementation, the testing assembly further includes a ground-penetrating radar (GPR) coupled to the base, the GPR generates and transmits subsurface images to a processing device and the processing device determines, as a function of the subsurface images, at least one of a compaction level of the soil or a moisture level of the soil.

In an example implementation combinable with any other example implementation, the plate includes an indentation at a center of the plate to support a weight applying the load and prevent the weight from shifting along the uppermost surface of the plate, allowing the load to be applied uniformly over a period of compaction.

In an example implementation combinable with any other example implementation, rotation of the studs changes an elevation of the plate without changing an elevation of the screws with respect to the base.

In an example implementation combinable with any other example implementation, the threaded studs include threaded knobs, each of the threaded knobs spaced apart equidistantly from one another.

In an example implementation, a method includes obtaining a testing apparatus that includes a base, threaded studs, and a plate. The base includes a body defining a flat surface and apertures each arranged to receive an electrode extending through a respective one of the apertures into soil disposed beneath the base. The threaded studs are rotationally coupled to the base and extend from the base normal with respect to the flat surface of the base. The plate is threadedly coupled to the studs such that rotation of the studs changes an elevation of the plate with respect to the base. The plate includes a lowermost surface facing the base and coupled to an end of each electrode such that, as the plate changes in elevation with respect to the base, each electrode moves through its respective aperture, changing a position of each electrode with respect to the soil. The method also includes placing a sample specimen inside a beaker. The method also includes placing the soil inside the beaker and on the sample specimen. The method also includes placing the testing apparatus on the soil with at least one electrode extending into the soil. The method also includes placing a weight on the plate to apply a load on the testing apparatus, allowing the testing apparatus to compact the soil under the load as each electrode detects a parameter of the sample specimen or the soil.

In an example implementation combinable with any other example implementation, the method further includes including rotating the threaded studs as the testing apparatus compacts the soil, moving each electrode with respect to the base to maintain a desired distance between a tip of each electrode and the sample specimen.

What is claimed is:

1. A testing assembly, comprising:

a beaker;

a sample holder disposed at a bottom surface of the beaker;

soil disposed within the beaker and on the sample holder;

a sample specimen disposed on the sample holder;

a three-electrode testing assembly disposed partially within the beaker and on the soil, the three-electrode testing assembly comprising:

a base comprising a body defining a flat surface arranged to bear against and compact the soil, the base defining a plurality of apertures each arranged to receive an electrode extending through a respective one of the plurality of apertures into the soil;

a plurality of threaded knobs rotationally coupled to the base and extend from the base normal with respect to the flat surface of the base; and a plate configured to be threadedly coupled to the plurality of threaded knobs such that rotation of the plurality of threaded knobs changes an elevation of the plate with respect to the base, the plate comprising a lowermost surface facing the base and an uppermost surface facing away from the base and arranged to receive a load, wherein the lowermost surface is coupled to an end of each electrode such that, as the plate changes in elevation with respect to the base, each electrode moves through its respective aperture, changing a position of each electrode with respect to the soil;

an electrochemical analyzer electrically coupled to each electrode and configured to process information received from each electrode and determine, as a function of the information, an electrochemical corrosion of the sample specimen; and a laser assembly, comprising:

a laser emitter coupled to an outer wall of the beaker and comprising an electronic display; and a laser reflector coupled to the plate and aligned with the laser emitter such that a laser emitted from the laser emitter reflects back to the laser emitter, allowing the laser emitter to detect the reflected laser and determine, as a function of the reflected laser, a distance between the laser emitter and the laser reflector.

2. The testing assembly of claim 1, wherein the laser emitter comprises a microcontroller, an electronic display, and a power source configured to power the electronic display, the microcontroller configured to determine the distance as the distance changes as the three-electrode testing assembly compacts the soil under the load, and the electronic display configured to display the distance in real time.

3. The testing assembly of claim 2, wherein the microcontroller is configured to determine, as a function of the determined distance, when a reduction in distance stabilizes, indicating that compaction is completed, and the laser reflector further comprises a speaker configured it emit a sound when the compaction is completed.

4. The testing assembly of claim 1, wherein the three-electrode testing assembly comprises a ground-penetrating radar (GPR) coupled to the base, the GPR configured to generate and transmit subsurface images to a processing device and the processing device is configured to determine, as a function of the subsurface images, at least one of a compaction level of the soil or a moisture level of the soil.

5. The testing assembly of claim 1, wherein the plate comprises an indentation at a center of the plate to support a weight applying the load and prevent the weight from shifting along the uppermost surface of the plate, allowing the load to be applied uniformly over a period of compaction.

6. A testing apparatus, comprising:

a base comprising a body defining a flat surface and a plurality of apertures each arranged to receive an electrode extending through a respective one of the plurality of apertures into soil disposed beneath the base;

a plurality of threaded studs configured to be rotationally coupled to the base and extend from the base normal with respect to the flat surface of the base; and a plate configured to be threadedly coupled to the plurality of threaded studs such that, with the testing apparatus assembled, rotation of the plurality of threaded studs changes an elevation of the plate with respect to the base, the plate comprising a lowermost surface facing the base and an uppermost surface facing away from the base and arranged to receive a load, wherein the lowermost surface is arranged to be coupled to an end of each electrode such that, as the plate changes in elevation with respect to the base, each electrode moves through its respective aperture, changing a position of each electrode with respect to the soil.

7. The testing apparatus of claim 6, further comprising a beaker configured to hold a sample with the soil inside the beaker and on the sample, the body of the base defining a flat surface arranged to bear against and compact the soil.

8. The testing apparatus of claim 7, wherein the body comprises a circular body defining a diameter corresponding with an inner diameter of the beaker such that the circular body is movable, with the flat surface parallel with respect to a base of the beaker, along the beaker to allow the circular body to move toward the base of the beaker and compact, under the load, the soil between the sample, the flat surface, and an inner wall of the beaker.

9. The testing apparatus of claim 8, further comprising a sample holder arranged to rest on the base of the beaker and comprising an indentation that holds the sample and prevents the sample from shifting along an upper surface of the sample holder.

10. The testing apparatus of claim 7, wherein the testing apparatus comprises a three-electrode testing assembly, and each electrode is electrically coupled to an electrochemical analyzer configured to process information received from each electrode and determine, as a function of the information, an electrochemical corrosion of the sample.

11. The testing apparatus of claim 10, wherein the plurality of apertures comprises four or more apertures, comprising a first aperture configured to receive a reference electrode, a second aperture configured to receive a working electrode, a third aperture configure to receive a counter electrode, and a further aperture configured to receive an instrument comprising at least one of a thermocouple or a pH measurement instrument.

12. The testing apparatus of claim 7, further comprising a laser assembly, comprising:

a laser emitter arranged to be coupled to an outer wall of the beaker and comprising an electronic display; and a laser reflector arranged to be coupled to the plate and aligned with the laser emitter such that a laser emitted from the laser emitter reflects back to the laser emitter, allowing the laser emitter to detect the reflected laser and determine, as a function of the reflected laser, a distance between the laser emitter and the laser reflector to determine a distance that the soil compacts under the load.

13. The testing apparatus of claim 12, wherein the laser emitter comprises a microcontroller, an electronic display, and a power source configured to power the electronic display, the microcontroller configured to determine the distance as the distance changes as the three electrode testing assembly compacts the soil under the load, and the electronic display configured to display the distance in real time.

14. The testing apparatus of claim 12, wherein the microcontroller is configured to determine, as a function of the determined distance, when a reduction in distance stabilizes, indicating that compaction is completed, and the laser reflector further comprises a speaker configured it emit a sound when the compaction is completed.

15. The testing apparatus of claim 6, further comprising a ground-penetrating radar (GPR) coupled to the base, the GPR configured to generate and transmit subsurface images to a processing device and the processing device is configured to determine, as a function of the subsurface images, at least one of a compaction level of the soil or a moisture level of the soil.

16. The testing apparatus of claim 6, wherein the plate comprises an indentation at a center of the plate to support a weight applying the load and prevent the weight from shifting along the uppermost surface of the plate, allowing the load to be applied uniformly over a period of compaction.

17. The testing apparatus of claim 6, wherein rotation of the studs changes an elevation of the plate without changing an elevation of the screws with respect to the base.

18. The testing apparatus of claim 6, wherein the plurality of threaded studs comprises a plurality of threaded knobs, each of the plurality of threaded knobs spaced apart equidistantly from one another.

19. A method, comprising:

obtaining a testing apparatus comprising:

a base comprising a body defining a flat surface and a plurality of apertures each arranged to receive an electrode extending through a respective one of the plurality of apertures into soil disposed beneath the base;

a plurality of threaded studs rotationally coupled to the base and extending from the base normal with respect to the flat surface of the base; and a plate threadedly coupled to the plurality of studs such that rotation of the plurality of studs changes an elevation of the plate with respect to the base, the plate comprising a lowermost surface facing the base and coupled to an end of each electrode such that, as the plate changes in elevation with respect to the base, each electrode moves through its respective aperture, changing a position of each electrode with respect to the soil;

placing a sample specimen inside a beaker;

placing the soil inside the beaker and on the sample specimen;

placing the testing apparatus on the soil with at least one electrode extending into the soil; and placing a weight on the plate to apply a load on the testing apparatus, allowing the testing apparatus to compact the soil under the load as each electrode detects a parameter of the sample specimen or the soil.

20. The method of claim 19, further comprising rotating the threaded studs as the testing apparatus compacts the soil, moving each electrode with respect to the base to maintain a desired distance between a tip of each electrode and the sample specimen.

* * * * *